US006596762B2

(12) United States Patent
Sokol

(10) Patent No.: US 6,596,762 B2
(45) Date of Patent: Jul. 22, 2003

(54) ANTIOXIDANT COMPOSITIONS AND USE FOR TREATMENT OF HEPATIC STEATOSIS AND STEATOHEPATITIS

(75) Inventor: Ronald J. Sokol, Denver, CO (US)

(73) Assignee: The Regents of The University of Colorado, Boulder, CO (US)

( * ) Notice: Subject to any disclaimer, the term of this patent is extended or adjusted under 35 U.S.C. 154(b) by 0 days.

(21) Appl. No.: 10/150,512

(22) Filed: May 17, 2002

(65) Prior Publication Data

US 2002/0183382 A1 Dec. 5, 2002

Related U.S. Application Data

(60) Provisional application No. 60/292,142, filed on May 17, 2001.

(51) Int. Cl.$^7$ .................. A01N 43/16; A01N 31/04; A01N 59/02
(52) U.S. Cl. .................. 514/458; 514/725; 424/702
(58) Field of Search .................. 424/702; 514/458, 514/725

(56) References Cited

U.S. PATENT DOCUMENTS

| | | | |
|---|---|---|---|
| 4,619,829 A | 10/1986 | Motschan | 424/128 |
| 5,326,757 A | 7/1994 | Demopoulos | 514/167 |
| 5,332,579 A | 7/1994 | Umbdenstock | 424/639 |
| 5,364,644 A | 11/1994 | Walaszek et al. | 514/574 |
| 5,763,435 A | 6/1998 | Setchell | 514/182 |
| 5,955,456 A | 9/1999 | Prato et al. | 514/182 |
| 6,069,167 A | 5/2000 | Sokol | 514/458 |
| 6,075,132 A | 6/2000 | Mandai et al. | 536/5 |
| 6,136,859 A * | 10/2000 | Henriksen | 514/561 |
| 6,180,139 B1 | 1/2001 | Hsia et al. | 424/464 |
| 6,218,437 B1 | 4/2001 | Chojkier | 514/731 |

FOREIGN PATENT DOCUMENTS

| | | |
|---|---|---|
| WO | WO 98/41216 | 9/1998 |
| WO | WO 00/62774 | 10/2000 |

OTHER PUBLICATIONS

Argao et al., *Pediatr. Res.*, 31:146–150 (1992).
Burk, *J. Nutr.* 119:1051:1054 (1989).
Database CAPLUS on STN, Abstract No. 1995:470793, Chen et al., Protection of Vitamin E, Selenium, Torlox C, Ascorbic Acid Palmitate, Acetylcysteine, Coenzyme Q0, Coenzyme Q10, Beta–carotene Canthaxanthin, and (+)_– Catechin Against Oxidative Damage to Rat Blood and Tissues in Vivo, abstract, Free Radical Bio. Med., 18(5) 1995.
Database WPIDS on STN, Abstract No. 95–044272, Ploch, Capsule for Active Detoxification of Body Cells Contg. Vitamin E, Beta Carotene, Selenium and Zinc as Free Radical Scavengers, abstract, DE 4322070 Al (Ploch E.M.) Jan. 12, 1995.
Database CAPLUS on STN, Abstract No. 1993:508953, Chen et al., Protection by Vitamin E, Selenium, Beta–carotene Against Oxidative Damage in Rat Liver Slices and Homogenate, Abstract Free Radical Bio. Med., 14(5), 1993.
Day, *Gastroenterology*, 114:842–45 (1998).
Goff et al., Mitochondrial Lipid Peroxidation Accompanies Intravenous Taurochenodeoxycholic Acid–Induced Hepatic Injury in the Rat, Abstract Amer. Gastroenterological Assn., New Orleans, LA, May 15, 1994.
Rotruck et al., *Science* 179:588–590 (1973).
Shivaram et al., Idebenone Inhibits Taurochenodeoxycholic Acid Toxicity and Reduces Oxidant Stress in Isolated Rat Hepatocytes, Abstract Meetings of the AGA, AASLD at Digestive Disease Week, San Diego, CA May 14, 1995.
Sokol et al., *J. Pediatr.*, 3:830–836 (1987).
Sokol et al., Free Radical Alteration of Hepatic Mitochondrial Lipids in End–Stage Liver Disease, Abstract Amer. Pediatric Society, Society for Pediatric Research, 1993, Abstract 25524.
Sokol e t al., *Hepatology*, 17:869–881 (1993).
Sokol et al., *Gastroenterology*, 93:975–85 (1987).
Sokol et al., *The Lancet*, 338:212–216 (1991).
Sokol et al., Taurochenodeoxycholic Acid Hepatotoxicity is Associated with Hepatocyte Hydroperoxide Generation and Mitochondrial Lipid Peroxidation, Abstract Joint Meeting of North Amer. Society for Pediatric Gastroenterology and Nutrition and the European Society for Paediatric Gastroenterology and Nutrition, Houston, TX Oct. 10, 1994.
Sokol et al., Vitamin E Reduces Oxidant Injury to Hepatic Mitochondria Caused by Intravenous Taurochenodeoxycholic Acid in the Rat, Abstract Amer. Liver Foundation, Chicago, IL Nov. 11, 1994.
Sokol et al., *Gastroentrology*, 104:1727–1735 (1993).
Sokol et al., *Gastroenterology*, 109:1249–1256 (1995).
Sokol et al., *Hepatology* 34(2):277A (2001).
Sokol et al., *J. Lipid Res.*, 32:1349–1357 (1991).
Sokol, *J. Pediatr.*, 136:711–713 (2000).
Sokol et al., Evidence of Free Radical Generation in Bile Acid Toxicity to Isolated Rat Hepatocytes, Abstract Amer. Assn. for the Study of Liver Diseases, Chicago, IL Oct. 31, 1992.
Winklhofer–Roob et al., Increased Generation of Hydrogen Peroxide by Isolated Rat Hepatic Mitochondria Exposed to Chenodeoxycholic Acid, Abstract Amer. Assn. for the Study of Liver Diseases, Chicago, IL Nov. 11, 1994.
Winklhofer–Roob et al., Dose–Dependent Increase in Hydrogen Peroxide Generation by Rat Hepatic Mitochondria Exposed to Chenodeoxycholic Acid and its Attenuation by Catalase, Abstract North Amer. Society for Pediatric Gastroenterology and Nutrition, Chicago, IL Nov. 3, 1995.
Yerushalmi et al., *Hepatology* 33:616–26 (2001).

* cited by examiner

Primary Examiner—Alton N. Pryor
(74) Attorney, Agent, or Firm—Sheridan Ross P.C.

(57) ABSTRACT

A composition and method for treating hepatic steatosis, steatohepatitis, and liver diseases associated with or characterized by these conditions. The composition consists essentially of defined amounts of soluble vitamin E, mixed carotenoids and selenium and in one aspect, can include at least one additional agent for the treatment of these conditions.

28 Claims, No Drawings

ANTIOXIDANT COMPOSITIONS AND USE FOR TREATMENT OF HEPATIC STEATOSIS AND STEATOHEPATITIS

CROSS-REFERENCE TO RELATED APPLICATIONS

This application claims priority under 35 U.S.C. §119(e) to U.S. Provisional Application Ser. No. 60/292,142, filed May 17, 2001, which is incorporated herein by reference in its entirety.

GOVERNMENT SUPPORT

This invention was made in part using government support under NIH Grant No. DK38446, awarded by the National Institutes of Health. The government has certain rights to this invention.

FIELD OF THE INVENTION

The present invention provides formulations and methods for preventing and treating liver injury that occurs in hepatic steatosis and steatohepatitis, as well as diseases associated with these conditions, including, but not limited to, nonalcoholic steatohepatitis. The method includes the administration of a composition that includes selected antioxidant compounds.

BACKGROUND OF THE INVENTION

Hepatic steatosis (fatty liver) and steatohepatitis (fatty liver with inflammation or scarring) are two forms of the fatty liver disease that develops in children and adults, frequently associated with being overweight or obese. This disease develops in at least 10–20% of adolescents and adults that are obese and in 5–10% of those that are overweight. This type of liver disease is often referred to as non-alcoholic steatohepatitis (NASH), because it occurs in the absence of a significant amount of alcohol intake. Currently, over 35% of the US population of adults and adolescents are overweight or obese, so this liver disease is probably the most common liver disease in the US and other developed countries. NASH has now been shown to lead to fibrosis (scarring) in at least 20–30% of patients who have undergone liver biopsies and is an increasing reason for patients to be evaluated for liver transplantation because of liver failure. Since obesity is now developing in childhood at an alarmingly increasing rate, NASH will probably be even more common in adults in the next decade, and will most likely become a more frequent cause of cirrhosis in adults and as an indication for liver transplantation.

The cause of NASH is not clearly understood, however, the combination of obesity, which causes the build-up of fat in the liver, and a second insult are proposed to lead to NASH from a benign form of fatty liver (*Gastroenterology* 1998; 114:842–45). This secondary insult is now felt by many researchers in the field (see Detailed Description below) to be caused by an additional oxidant stress (free radical damage) to the liver caused by abnormal metabolism of the cell containing fat, small increases of iron deposited in the liver in certain individuals, blood-born chemicals (cytokines) released from other tissues that contain fat, or increased production of free radicals by mitochondria (the energy producing part of each cell) in liver cells that contain fat. Whatever the cause of the oxidant stress, it appears to accelerate damage to the liver cells and stimulate the production of scar tissue (fibrosis) by certain cells in the liver (hepatic stellate cells) that leads to the fibrosis and eventual cirrhosis of the liver.

Dr. Joel Lavine of San Diego has published a pilot trial using only vitamin E in children with NASH and showed that serum AST and ALT were reduced during therapy. There were no liver biopsies performed after treatment to determine if there was an effect on hepatic fibrosis or the extent of steatosis during or after therapy (Lavine, June 2000, *J. Pediatr.* 136:711–713). This treatment used oral Vitamin E at a dose between 400 and 1200 IU per day. Lavine et al. did not use compounds other than Vitamin E.

U.S. Pat. No. 6,136,859, issued Oct. 24, 2000, to Henriksen describes the a pharmaceutical composition comprising organic or inorganic selenium, β-carotene or vitamin A, ascorbic acid, α-tocopherol, methionine and coenzyme Q10 with a pharmaceutically acceptable carrier for treating liver diseases including steatohepatitis. The selenium is provided in a range of from 0.01–0.1% by weight of the composition or 0.05 mg–0.15 mg selenium per dose. The β-carotene is provided in a range of from 0.65–0.85% by weight of the composition or 3 mg–5 mg β-carotene per dose. The α-tocopherol is provided in a range of from 8.55–9.55% by weight of the composition or 40 mg–87 mg α-tocopherol per dose.

U.S. Pat. No. 6,180,139, issued Jan. 30, 2001 to Hsia et al. describes a method to treat NASH comprising administering compositions composed of lechithin, antioxidants (at least vitamin C or vitamin E, and may also include vitamin A and/or selenium) and vitamin B complex. In this composition, the antioxidants and vitamin B complex is provided at a total dosage of 675 to 4050 mg per daily dose. In the only example, vitamin E is provided at about 71.4 units (mg) per dose, β-carotene is provided at about 5 units (mg) per dose, and selenium is provided at about 15.6 units (mg) of selenium yeast at 1600 μg/g. The example composition also included vitamin C, vitamin B complex, and other components.

PCT Publication No. WO 00/62774, published Oct. 26, 2000 describes a method to treat various disorders, including hepatic steatosis, with compositions comprising isoflavonoids.

PCT Publication No. WO 98/41216, published Sep. 24, 1998 describes a method to treat hepatic steatosis using a bile acid sequestrant (e.g., cholestyramine), optionally in combination with omega-3 polyunsaturated fatty acids, short-chain fatty acids, glutamine, arginine, an antioxidant, ribonucleic acids or nucleotides. Antioxidants include vitamins A, C, E and β-carotene but dosage is not specified.

U.S. Pat. No. 6,218,437, issued Apr. 17, 2001 to Chojkier describes methods for treatment of viral hepatitis C by administering vitamin E and other compounds with antioxidant properties. The vitamin E is administered at a dose of from 800 units daily to 1600 units daily. This patent does not teach a method to treat hepatic steatosis.

U.S. Pat. No. 6,069,167, issued May 30, 2000 to Sokol describes the use of a combination of selected antioxidants to treat a different condition of the liver known as cholestasis. Cholestasis is characterized as a group of disorders in which bile flow in the liver is impaired or blocked. U.S. Pat. No. 6,069,167 describes the use of Vitamin E in an amount between 25 and 100 IU/kg/day, β-carotene in an amount between 0.5 and 5 mg/kg/day, and selenium in an amount between 1 and 5 μg/kg/day to treat cholestasis. Cholestasis is a completely different liver condition than hepatic steatosis which affects a completely different patient population than hepatic steatosis. Therefore, there is no expected correlation between a composition useful for the treatment of cholestasis and a composition useful for treatment of hepatic steatosis. U.S. Pat. No. 6,069,167 does not teach or suggest any composition useful for the treatment of hepatic steatosis.

U.S. Pat. No. 5,763,435, issued Jun. 9, 1998 to Setchell describes the use of ursodeoxycholic acid to treat a disorder, including cancers and liver disorders.

U.S. Pat. No. 6,075,132, issued Jun. 13, 2000 to Mandai et al. describes ursodeoxycholic acid derivatives, which is described as being useful for the preparation of medicines.

U.S. Pat. No. 5,955,456, issued Sep. 21, 1999 to Prato et al. describes injectable compositions comprising urosdeoxycholic acid or tauroursodeoxycholic acid, which is described as being useful for the treatment of various pathological conditions of the liver.

There are currently no effective treatments for NASH, except for the recommendation that patients lose weight. With weight loss, abnormal elevations of liver enzymes released into the blood by the liver in NASH are reduced, however, the effect of weight loss on scarring and the amount of fat in the liver have not been well studied. Unfortunately, it is a fact that it is very difficult for obese and overweight people to lose and keep off this extra weight. Therefore, new, effective, non-toxic therapies that are designed to reduce liver injury and prevent or reduce scarring in the liver in patients with NASH are certainly needed.

SUMMARY OF THE INVENTION

One embodiment of the present invention relates to a pharmaceutical composition for treatment of a patient that has or is at risk of developing hepatic steatosis or steatohepatitis, the composition consisting essentially of: (a) soluble vitamin E in an amount of between about 10 international units per kilogram body weight of the patient per day (IU/kg/day) and about 100 IU/kg/day; (b) mixed carotenoids in an amount of between about 0.1 milligram per kilogram body weight of the patient per day (mg/kg/day) and about 1 mg/kg/day; and, (c) selenium in an amount of between about 0.5 microgram per kilogram body weight of the patient per day ($\mu$g/kg/day) and about 3 $\mu$g/kg/day. In one aspect, the vitamin E is D-alpha tocopheryl polyethylene glycol-1000 succinate, the mixed carotenoids comprise natural source water-dispersible $\beta$-carotene, and/or the selenium is sodium selenite pentahydrate.

In one aspect, the composition consists essentially of: (a) soluble vitamin E in an amount of between about 25 IU/kg/day and about 75 IU/kg/day, and in another aspect, between about 25 IU/kg/day and about 50 IU/kg/day; (b) mixed carotenoids in an amount of between about 0.2 mg/kg/day and about 0.5 mg/kg/day; and, (c) selenium in an amount of between about 1 $\mu$g/kg/day and about 2 $\mu$g/kg/day. In another aspect, the composition consists essentially of: (a) soluble vitamin E at a concentration of from about 20 IU vitamin E per milliliter of the composition (20 IU/ml) to about 75 IU/ml; (b) mixed carotenoids at a concentration from about 0.1 mg per ml of the composition (0.1 mg/ml) to about 0.75 mg/ml; and, (c) selenium at a concentration of from about 1 $\mu$g per ml of the composition (1 $\mu$g/ml) to about 5 $\mu$g/ml.

Another embodiment of the present invention relates to a pharmaceutical composition for treatment of a patient that has or is at risk of developing hepatic steatosis or steatohepatitis, the composition comprising: (a) soluble vitamin E in an amount of between about 10 international units per kilogram body weight of the patient per day (IU/kg/day) and about 100 IU/kg/day; (b) mixed carotenoids in an amount of between about 0.1 milligram per kilogram body weight of the patient per day (mg/kg/day) and about 1 mg/kg/day; (c) selenium in an amount of between about 0.5 microgram per kilogram body weight of the patient per day ($\mu$g/kg/day) and about 3 $\mu$g/kg/day; and, (d) an agent effective for the treatment of liver injury resulting from hepatic steatosis and related disorders. In one aspect, the agent of (d) is chosen from ursodeoxycholic acid, tauro-ursodeoxycholic acid, or a derivative of either ursodeoxycholic acid or tauro-ursodeoxycholic acid. In a preferred embodiment, the agent is ursodeoxycholic acid or a derivative thereof. The amounts and forms of vitamin E, mixed carotenoids, and selenium can be varied in this composition as described above.

Another embodiment of the present invention relates to a method of treating liver injury resulting from hepatic steatosis or steatohepatitis in a patient. The method includes administering to a patient that has or is at risk of developing hepatic steatosis or steatohepatitis a pharmaceutical composition consisting essentially of soluble Vitamin E, mixed carotenoids and selenium. In one embodiment, the method is used to treat a patient that has or is at risk of developing nonalcoholic steatohepatitis (NASH). In one aspect, the composition consists essentially of: (a) soluble vitamin E in an amount of between about 10 international units per kilogram body weight of the patient per day (IU/kg/day) and about 100 IU/kg/day; (b) mixed carotenoids in an amount of between about 0.1 milligram per kilogram body weight of the patient per day (mg/kg/day) and about 1 mg/kg/day; and, (c) selenium in an amount of between about 0.5 microgram per kilogram body weight of the patient per day ($\mu$g/kg/day) and about 3 $\mu$g/kg/day. Various embodiments of the composition are also encompassed as described above.

Yet another embodiment of the present invention relates to a method of treating liver injury resulting from hepatic steatosis or steatohepatitis in a patient. The method includes administering to a patient that has or is at risk of developing hepatic steatosis or steatohepatitis a pharmaceutical composition comprising soluble Vitamin E, mixed carotenoids, selenium, and at least one additional agent for the treatment of liver injury resulting from hepatic steatosis or steatohepatitis. In one embodiment, the composition comprises: (a) soluble vitamin E in an amount of between about 10 international units per kilogram body weight of the patient per day (IU/kg/day) and about 100 IU/kg/day; (b) mixed carotenoids in an amount of between about 0.1 milligram per kilogram body weight of the patient per day (mg/kg/day) and about 1 mg/kg/day; (c) selenium in an amount of between about 0.5 microgram per kilogram body weight of the patient per day ($\mu$g/kg/day) and about 3 $\mu$g/kg/day; and (d) the at least one additional agent for the treatment of liver injury resulting from hepatic steatosis or steatohepatitis. In one aspect, the agent for the treatment of hepatic steatosis or steatohepatitis is chosen from ursodeoxycholic acid, tauro-ursodeoxycholic acid or a derivative thereof. In a particular aspect, the agent for the treatment of hepatic steatosis or steatohepatitis is ursodeoxycholic acid or a derivative thereof.

DETAILED DESCRIPTION OF THE INVENTION

The present invention generally relates to compositions and methods to inhibit the biological events associated with the development and progression of hepatic steatosis and steatohepatitis and/or the symptoms associated with these conditions. More particularly, it is an object of the present invention to provide safe, inexpensive, non-surgical methods for the prevention and treatment of liver injury that occurs in hepatic steatosis, including, but not limited to, nonalcoholic steatohepatitis (NASH).

It is also an object of the present invention to provide compositions which are ideally suited for this therapeutic goal. Other objects of the present invention will be readily apparent to those of ordinary skill in the appropriate art.

In accordance with one aspect of the present invention, there is provided a method of preventing and treating liver damage caused by hepatic steatosis, steatohepatitis and related liver diseases, including, but not limited to, nonalcoholic steatohepatitis. The method is useful for the treatment of mammalian organisms, and particularly human beings (together, hereafter referred to as "patients"), and includes the step of administering to patients that have or are at risk of developing hepatic steatosis a pharmaceutical formulation (composition) comprising the following compounds: soluble Vitamin E, mixed carotenoids (e.g., beta carotene), and selenium, each of said compounds of the formulation being present in an amount effective to prevent or treat liver injury that occurs in hepatic steatosis. In one embodiment, the pharmaceutical formulation of the present invention consists essentially of soluble Vitamin E, mixed carotenoids, and selenium. In another embodiment, the pharmaceutical formulation of the present invention consists essentially of soluble Vitamin E, mixed carotenoids, and selenium and at least one additional agent that is useful for treating hepatic steatosis, steatohepatitis and related liver diseases, including, but not limited to, ursodeoxycholic acid, tauro-ursodeoxycholic acid, and derivatives thereof.

The antioxidants in this mixture were chosen for the following scientific reasons. Vitamin E has been shown to be a potent antioxidant in hepatocytes and in hepatic mitochondria in the present inventor's laboratory. The present inventor has also recently shown that alpha tocopherol (vitamin E) will prevent oxidative stress and hepatocyte cell death that occurs in liver cells that are fat-laden and exposed to relatively low concentrations of bile acids (*Gastroenterology* 2000;122 (Suppl) A642; see also Example 1). Briefly, fat-laden hepatocytes were isolated from the Zucker rat model of hepatic steatosis and from lean littermate Zucker rats. The fat-laden hepatocytes had a markedly increased susceptibility to cell necrosis when exposed to toxic bile acids than the lean hepatocytes, and conversely underwent less apoptosis. Without being bound by theory, the present inventor believes that the fatty liver is more prone to hepatocyte necrosis and thus is at risk for severe injury from minor and major insults. These data show that antioxidants are indicated to be of particular use in limiting injury to fat-laden liver cells. Studies from the present inventor's laboratory have shown that the effect of vitamin E is probably mediated through reduction of free radical production from mitochondria (Yerushalmi et al., *Hepatology* 2001; 33:616–26, incorporated herein by reference in its entirety).

Beta carotene and other carotenoids also function as antioxidants in tissues with low oxygen content (such as the liver) and the present inventor has shown beta carotene to have a protective role in hepatic mitochondria that prevents processes that generate oxygen free radicals (unpublished data). In isolated human and rat liver mitochondria, the present inventor has shown that beta carotene markedly diminishes the production of free radicals and protects the mitochondria from swelling and injury induced by toxic bile acids. (Sokol et al., *Hepatology* 2001;34(2):277A, incorporated herein by reference in its entirety).

Selenium is included in this mixture to provide this critical metal for the function of the enzyme glutathione peroxidase, which is a key antioxidant enzyme in mitochondria and in the rest of the hepatocyte.

The present inventor's studies in isolated hepatic mitochondria are the first of which the present inventor is aware that demonstrate that beta carotene protects mitochondria from processes shown to stimulate free radical production in hepatic mitochondria. The present inventor has previously shown that vitamin E also has this protective effect. It is believed that the combination of the antioxidants disclosed herein, in the amounts disclosed herein, will provide more robust protection against free radical generation in hepatic mitochondria during hepatic steatosis, thus preventing the progression of this condition to steatohepatitis.

While some of the components of the formulation of the present invention are available in common multi-vitamin supplements, they are not provided in the combinations or in the quantities believed to be necessary for the treatment of hepatic steatosis, steatohepatitis and related liver diseases as disclosed herein, nor are they likely to be administered in a pattern sufficient to maintain their levels in the body consistently through a 24-hour period. More particularly, in compositions described for the treatment of hepatic steatosis prior to the invention, if vitamin E or carotenoids are included, the amounts of vitamin E and mixed carotenoids described are significantly lower than the amounts of the same components described herein. By way of example, in one embodiment of the invention, assuming a person of average body weight of about 75 kg is to be treated, a single daily dose could include vitamin E at a dose of 750 IU–7500 IU/day and mixed carotenoids at a dose of 7.5 mg–75 mg/day. The present inventor is not aware of any suggestion to use these ingredients in the disclosed combination and dosage amounts to treat liver injury caused by hepatic steatosis, steatohepatitis and related liver diseases.

Moreover, while not wishing to be bound by theory, it is believed that the provision of solubilizing vitamin E (e.g., TPGS) will solubilize the beta carotene to allow its absorption. TPGS has been shown to form micelles in the absence of bile salts and can improve the intestinal absorption of other fat-soluble substances, such as cyclosporin (Sokol et al., *Lancet* 1991; 338:212–215) and Vitamin D (Argao et al., *Pediatr Res* 1992; 31:146–150), when bile flow is impaired. Thus, the water-insoluble beta carotene will have enhanced absorption from the intestine when solubilized in a solution of TPGS. Without this solubilization, beta carotene is very poorly absorbed in hepatic steatosis, steatohepatitis and related liver diseases.

This invention is unique compared to the vitamin E treatment used in the study of Lavine (see Background of the Invention) because of the balanced combination of antioxidants used to treat hepatic steatosis and/or steatohepatitis in the present invention, because of the solubilization of the other ingredients provided for by the soluble form of vitamin E (TPGS), and the improvement in intestinal absorption of these antioxidants provided by the action of the TPGS. This invention will be useful for physicians and other health care providers who care for patients with NASH, an increasingly important medical problem in developed countries, for which there is no effective pharmacologic therapy. It is believed that the antioxidant solution of the present invention will be useful in overweight and obese patients, to prevent the conversion from benign hepatic steatosis to the more damaging steatohepatitis. The latter condition involves gradual progressive fibrosis in the liver, with the eventual development of cirrhosis and end-stage liver disease. The present invention will prevent free radical damage to the liver and reduce the generation of lipid peroxide products which are formed in the inflamed and injured liver. These substances are believed to be involved in the process of fibrogenesis by directly stimulating hepatic stellate cells to produce collagen and other extracellular matrix proteins that lead to fibrosis and cirrhosis of the liver.

Thus, a pharmaceutical formulation of the present invention essentially contains three antioxidants that function in separate ways and that will reduce oxidative stress in the hepatocyte and in hepatic mitochondria by a variety of complementary mechanisms. It is believed that this particular mixture of antioxidants in the amounts described herein is superior to any previously described compositions for the treatment of hepatic steatosis or steatohepatitis. It is noted that the doses of each antioxidant to be used in the composition of the invention have been shown to be non-toxic in animal experiments and in published human studies unrelated to the method of use in this invention.

The pharmaceutically active antioxidant containing compositions of the present invention have a formulation that includes Vitamin E, beta carotene and selenium. In a preferred embodiment of the present invention, there is provided a pharmaceutically active antioxidant containing composition which includes Vitamin E in an amount such that there is delivered to a patient between about 10 international units per kilogram body weight of the patient per day (IU/kg/day) and about 100 IU/kg/day; mixed carotenoids in an amount of between about 0.1 milligrams (mg)/kilogram (kg)/day and about 1 mg/kg/day; and selenium (e.g., as sodium selenite pentahydrate) in an amount of between about 0.5 micrograms ($\mu$g)/kg/day and about 3 $\mu$g/kg/day. In one embodiment, the composition is capable of being administered in a single 24-hour period and the composition is effective in the treatment of liver injury resulting from hepatic steatosis, steatohepatitis and related liver diseases in patients (e.g., the composition inhibits the biological mechanisms associated with the liver injury and/or reduces at least one physiological symptom of the condition).

In one aspect, the invention consists of a formulation of antioxidants that include: a water soluble form of vitamin E (e.g., D-alpha tocopheryl polyethelene glycol-1000 succinate, or TPGS) at a concentration from about 20 IU/ml to about 75 IU/ml; mixed carotenoids at a concentration from about 0.1 mg/ml to about 0.75 mg/ml; and selenium at a concentration of from about 1 $\mu$g/ml to about 5 micrograms/ml ($\mu$g/ml). Concentrations are described herein as an amount of the given compound per milliliter of the composition as a whole. This mixture of antioxidants are all targeted to the liver and will be well absorbed from the intestines even in the presence of significant liver dysfunction. This particular mixture of antioxidants provided in the indicated amounts is believed to be effective in preventing the fibrosis and cirrhosis of non-alcoholic steatohepatitis (NASH), thereby reducing the symptoms of the condition.

The soluble form of vitamin E is provided in the composition at a concentration from about 20 IU/ml to about 75 IU/ml. Reference to Vitamin E herein refers to any group of at least eight related fat-soluble compounds with similar biological anti-oxidant activity, and particularly includes alpha-tocopherol, but also includes other isomers of tocopherol and the related compound tocotrienol. According to the instant invention, the most preferred form of Vitamin E is water soluble D-alpha-tocopheryl polyethylene glycol-1000 succinate or TPGS (Eastman Chemical Corporation, Kingsport, Tenn.). Vitamin E (D-alpha tocopheryl polyethylene glycol-1000 succinate [TPGS] in the preferred embodiment) is broken down during digestion to yield alpha tocopherol which is the active antioxidant form. The use of D-alpha tocopheryl polyethylene glycol-1000 succinate preferred because this form of Vitamin E is uniquely water-soluble. Unfortunately, as a fat soluble vitamin, alpha tocopherol is probably not absorbed completely even in this form and a significant portion of the dosage ingested may be excreted. Thus, it is important that the amount of Vitamin E provided in each dosage be high enough to achieve the desired result. In general, alpha tocopherol and beta carotene enter cell membranes, including those of the mitochondria, and serve as lipoidal antioxidants scavenging hydroxyl, hydroperoxyl and other oxy radicals. The preferred form of Vitamin E, TPGS, is meant to aid in the ability of these two compounds to be absorbed by virtue of its solubilizing characteristics.

In one embodiment, the vitamin E is provided at a concentration of at least about 20 IU/ml, and in another embodiment, at least about 25 IU/ml, and in another embodiment, at least about 30 IU/ml, and in another embodiment, at least about 35 IU/ml, and in another embodiment, at least about 40 IU/ml, and in another embodiment, at least about 45 IU/ml, and in another embodiment, at least about 50 IU/ml, and in another embodiment, at least about 55 IU/ml, and in another embodiment, at least about 60 IU/ml, and in another embodiment, at least about 65 IU/ml, and in another embodiment, at least about 70 IU/ml, and in another embodiment, at a concentration of up to about 75 IU/ml. It is to be understood that the soluble vitamin E can be provided at a concentration range within any two of the above concentrations, such as 20-40 IU/ml, 35–55 IU/ml, 25–65 IU/ml, etc.

The mixed carotenoids are provided in the composition at a concentration of from about 0.1 mg/ml to about 0.75 mg/ml. The most preferred form of mixed carotenoids, and particularly, beta carotene, is natural source water-dispersible $\beta$-carotene (Henkel). Other forms of beta carotene can include water miscible beadlets (80% all trans and 20% cis isomer) as well as other natural forms. As is true with Vitamin E, the body's uptake of beta carotene is relatively slow and incomplete. Therefore the preferred Vitamin E form has been selected to solubilize the beta carotene to allow its absorption (see above). Fortunately, to combat liver injury caused by hepatic steatosis, steatohepatitis and related liver diseases, the ideal administration regimen for beta carotene is similar to that of Vitamin E. Furthermore, there is an efficient regulatory system in the intestinal mucosa and the liver that prevents the overproduction of Vitamin A from its precursor, beta carotene. Thus, the bulk of the administered beta carotene remains unchanged and serves as a lipoidal antioxidant that scavenges hydroperoxyl and singlet oxygen. There is, therefore, little or no possibility of hypervitaminosis. In addition, the beta carotene aids in the suppression of the metabolic oxidation of arachidonic acid.

In one embodiment, the mixed carotenoids are provided at a concentration of at least about 0.15 mg/ml, and in another embodiment, at least about 0.2 mg/ml, and in another embodiment, at least about 0.25 mg/ml, and in another embodiment, at least about 0.3 mg/ml, and in another embodiment, at least about 0.35 mg/ml, and in another embodiment, at least about 0.4 mg/ml, and in another embodiment, at least about 0.45 mg/ml, and in another embodiment, at least about 0.5 mg/ml, and in another embodiment, at least about 0.55 mg/ml, and in another embodiment, at least about 0.6 mg/ml, and in another embodiment, at least about 0.65 mg/ml, and in another embodiment, at least about 0.7 mg/ml, and in another embodiment, at a concentration of up to about 0.75 mg/ml. It is to be understood that the mixed carotenoids can also be provided at a concentration range within any two of the above concentrations, such as 0.3–0.5 mg/ml, 0.25–0.65 mg/ml, 0.1–0.3 mg/ml, etc.

The selenium is provided in the composition at a concentration of from about 1 µg/ml to about 5 µg/ml. Suitable forms of selenium can include sodium selenate, sodium selenite, selenomethionine, and selenium yeast. The most preferred form of selenium is sodium selenite pentahydrate (Ciba, Canada). Selenium functions as an antioxidant because it is an essential component of the selenium-dependent glutathione peroxidase, an enzyme that detoxifies lipid hydroperoxides and hydrogen peroxide. This enzyme is located intracellularly in the liver and also extracellularly around liver cells and in the circulating blood (Rotruck et al., Science 1973; 179:588–590). Additional selenoproteins may also have antioxidant properties (Burk, J. Nutr. 1989; 199:1051–1054).

In one embodiment, the selenium is provided at a concentration of at least about 1.5 µg/ml, and in another embodiment, at least about 2 µg/ml, and in another embodiment, at least about 2.5 µg/ml, and in another embodiment, at least about 3 µg/ml, and in another embodiment, at least about 3.5 µg/ml, and in another embodiment, at least about 4 µg/ml, and in another embodiment, at least about 4.5 µg/ml, and in another embodiment, at a concentration of up to about 5 µg/ml. It is to be understood that the selenium can also be provided at a concentration range within any two of the above concentrations, such as 1–3.5 µg/ml, 4–5 µg/ml, 2.5–4 µg/ml, etc.

In accordance with the discussion above, in one aspect of the invention, the pharmaceutically active antioxidant containing composition includes the correct amounts of each antioxidant such that the following amounts will be delivered to patients in need thereof: a formulation including Vitamin E to deliver between about 10 IU/kg/day and about 100 IU/kg/day; natural mixed carotenoids (e.g., beta carotene) to deliver between about 0.1 mg/kg/day and about 1 mg/kg/day, and selenium to deliver between about 0.5 micrograms (µg)/kg/day and about 3 µg/kg/day, wherein the composition can be administered in a 24-hour period and wherein the composition is effective in the treatment of hepatic steatosis, steatohepatitis and related liver diseases in a mammalian organism, particularly a human being, in need thereof. In one aspect, a preferred formulation of the present invention contains about 75 IU of Vitamin E (as D-alpha-tocopheryl polyethylene glycol-1000 succinate) per ml, about 0.75 mg mixed carotenoids per ml, and about 1.5 µg of selenium (as sodium selenite pentahydrate) per ml, or the appropriate amount based on the amount to be delivered to the patient as determined by one skilled in the art.

It is preferred that the antioxidants of the present invention be provided in a form which is as nearly pure as possible. In a preferred embodiment, the antioxidants are provided without noxious lubricants (sand, soaps, talc), fillers, colors, flavors, binders, dispersants or like adjuvants commonly employed as delivery excipients in the pharmaceutical industry. The antioxidant ingredients, as well as other ingredients in the formulation, may be administered individually, or in combination, in a pill or capsule form, in powdered form or in the form of a solution, slurry or dispersion. However, for convenience, and dosage consistency, as well as for assisting in the uniform administration of various dosages of the individual ingredients throughout a 24-hour period, it is advantageous and preferred that the ingredients described herein be admixed and administered together in a solution to be taken orally once or twice per day, or otherwise as necessary to treat hepatic steatosis, steatohepatitis, and/or liver disease associated with these conditions. It is most preferred that the formulation of the present invention be provided in the form of a solution to be taken orally.

The pharmaceutical formulation of the present invention can include, in one embodiment, in addition to the active antioxidant ingredients, a pharmaceutically acceptable carrier and/or excipient, although the use of many excipients is typically not preferred, as set forth above. When used, suitable excipients of the present invention include excipients or formularies that are capable of maintaining the antioxidant composition in an active form for storage and delivery to the patient. Some pharmaceutically acceptable carriers are controlled release formulations that are capable of slowly releasing a composition of the present invention into a patient.

The combination of the three ingredients described previously, namely mixed carotenoids (preferably as beta carotene), Vitamin E and selenium, are believed to provide for the prevention and/or treatment of liver injury and fibrosis in hepatic steatosis, steatohepatitis and related liver diseases. As previously described, it is believed that these ingredients help shut down the formation of free radicals and scavenge those free radicals that are produced.

In one aspect of the invention, the antioxidant formulation of the present invention can be formulated as follows: the soluble vitamin E (e.g., pure TPGS (Eastman Chemical Company, Kingsport, Tenn.)) in solid form is melted into a liquid state by heating to above 40° C. and stirring to ensure homogeneity. Weighed portions of the liquid TPGS are poured slowly into measured volumes of boiling sterile water, which are constantly stirred for 1 to 2 hours while cooling down to room temperature. Once at room temperature, to this 20% TPGS solution are added weighed portions of beta carotene and selenium while the mixture is stirred. The preferred form of beta carotene is natural source water dispersible P-carotene (Henkel) and of selenium is sodium selenite pentahydrate (Ciba, Canada). Alternatively, the beta carotene may be added to the TPGS while it is in its warmed, liquid state, then added to water, etc. The mixture is tested for shelf life, stability, and such tests well known to those skilled in the art. The above-described method is provided as an example. Adaptations to this process, particularly when different amounts and forms of the ingredients are used, will be apparent to those of skill in the art.

It is important to note that these formulations are not meant as a replacement of those ingredients naturally produced in the body and/or consumed in the diet, but rather represent a supplement designed to increase normal blood levels.

The present invention contemplates the preparation of a combination product that utilizes the novel antioxidant mixture oft e present invention plus at least one additional agent that is at least somewhat effective in the treatment of hepatic steatosis or steatohepatitis and diseases associated with or characterized by these conditions (e.g., NASH). Therefore, in one embodiment, the antioxidant formulation can include one or more additional agents that are useful for treating hepatic steatosis and related disorders. For example, two of such agents are ursodeoxycholic acid or tauro-ursodeoxycholic acid, and derivatives thereof Ursodeoxycholic acid and tauro-ursodeoxycholic acid are well known in the art and multiple derivatives of these agents have been described in the art (see Background section, for example). For Example, U.S. Pat. No. 5,763,435, incorporated herein by reference in its entirety, teaches "a sulfate of 3 alpha, 7 beta-dihydroxy-5 beta-cholan-24-oic acid (Ursodeoxycholic acid or "UDCA")" which include "monosulfate and disulfate esters of UDCA". U.S. Patent No 6,075,132, also incorporated herein by reference in its entirety, teaches derivatives of UDCA "haling an increased solubility in water", including ursodeoxycholic acid derivatives having a saccharide moiety as bonded to ursodeoxycholic acid via a spacer therebetween." Other agents that are useful for treating liver disease and especially hepatic steatosis and related disorders will be known to those of skill in the art and are intended to be encompassed by the present invention. The composition of the present invention includes an effective amount of ursodeoxycholic acid or tauro-ursodeoxycholic acid to provide a measurable benefit to the patient to be treated, and/or as has been established in the art for use of these compounds to treat liver diseases (e.g., see U.S. Pat. No. 5 763,435, supra, U.S. Pat. No. 6,075,132, supra, or U.S. Pat. No. 5,955,456, supra, each of which is incorporated herein by reference in its entirety).

The aforementioned compositions of the present invention can be particularly useful in the prevention and treatment of liver injury of any etiology caused by hepatic steatosis, steatohepatitis and related liver diseases, including, but not limited to, nonalcoholic steatohepatitis (NASH). They represent a balance of ingredients which serve not only to reduce the number of free radicals formed in the liver, but also to inhibit the metabolic oxidation of arachidonic acid. The more preferred formulations in accordance with the present invention also enhance the performance of the composition by transporting certain antioxidant ingredients in the formulation and by offering the formulation in a form suitable for long-term use. These compositions, when provided in sufficient dosage over a period of 24 hours, can be useful in the prevention and treatment of liver injury and fibrosis caused by hepatic steatosis, steatohepatitis and related liver diseases.

The pharmaceutical composition of the present invention will be typically administered orally once or twice daily, or more or less frequently as necessary, at a dose to achieve an intake of from about 10 IU/kg/day to about 100 IU/kg/day of vitamin E (e.g., alpha tocopherol (as TPGS)), from about 0.1 mg/kg/day to about 1 mg/kg/day of beta carotene as mixed carotenoids, and from about 0.5 µg/kg/day to about 3 µg/kg/day of selenium. Doses are described as an amount of compound per kilogram body weight of the patient per day.

Preferably, the dose of vitamin E in the formulation is sufficient to achieve an intake of any amount including or between about 10 IU/kg/day and about 100 IU/kg/day, and in one embodiment, between about 25 IU/kg/day and about 75 IU/kg/day, and in another embodiment, between about 25 IU/kg/day and about 50 IU/kg/day. It is to be understood that a sufficient amount of vitamin E can include any amounts and/or ranges intermediate to the above-described ranges in whole integers (e.g., 11 IU/kg/day, 12 IU/kg/day, 13 IU/kg/day, between 10–50 IU/kg/day, between 55–90 IU/kg/day, etc.).

The dose of mixed carotenoids is preferably sufficient to achieve an intake of any amount including or between about 0.1 mg/kg/day and 1 mg/kg/day, and in one embodiment, between about 0.2 mg/kg/day and about 0.5 mg/kg/day. It is to be understood that a sufficient amount of mixed carotenoids can include any amounts and/or ranges intermediate to the above-described ranges in increments of 0.1 mg/kg/day (e.g., 0.2 mg/kg/day, 0.3 mg/kg/day, 0.4 mg/kg/day, between 0.3–0.5 mg/kg/day, between 0.1–0.5 mg/kg/day, etc.).

Preferably, the dose of selenium in the formulation is sufficient to achieve an intake of any amount including or between about 0.5 µg/kg/day and about 3 µg/kg/day, and in one embodiment, between about 1 µg/kg/day and about 2 µg/kg/day. It is to be understood that a sufficient amount of selenium can include any amounts and/or ranges intermediate to the above-described ranges in increments of 0.25 µg/kg/day (e.g., 0.75 µg/kg/day, 1 µg/kg/day, 1.25 µg/kg/day, between 0.5–1.75 µg/kg/day, between 1.25–2.25 µg/kg/day, etc.)

Advantageously and preferably, the composition, in accordance with the present method is administered in one, or, if two, substantially equal dosages to a patient per day. Administration can be oral. One advantage of this mixture of antioxidants is that they are all targeted to the liver, they will be well absorbed from the intestines even in the presence of significant liver dysfunction or cirrhosis, and they are non-toxic in the doses used.

The antioxidant formulations of the instant invention can optionally contain reducing agents. Such reducing agents can be any suitable reducing agent that maintains components in reduced state. Such reducing agents include, for example, succinate, glutamate and glutathione.

Compositions of the present invention are administered to mammals and preferably, humans. Patients whom are suitable candidates for the method of the present invention include, but are not limited to, patients that have, or are at risk of developing (e.g., are predisposed to), hepatic steatosis, steatohepatitis, or a liver disease associated with or characterized by these conditions. Preferably, the compositions of the present invention inhibit or reduce a biological mechanism that is associated with the disease/condition, and/or reduce or eliminate at least one symptom associated with the disease/condition. As such, a therapeutic benefit is not necessarily a cure for a particular disease or condition, but rather, preferably encompasses a result which most typically includes alleviation of the disease or condition, elimination of the disease or condition, reduction of a symptom associated with the disease or condition, prevention or alleviation of a secondary disease or condition resulting from the occurrence of a primary disease or condition and/or prevention of the disease or condition. As used herein, to "treat" a disease refers to reducing the symptoms of the disease or reducing the biological/physiological mechanisms associated with the development and progression of the disease; reducing the occurrence of the disease, and/or reducing the severity of the disease. "Protecting" a patient with a disease can refer to the ability of a composition of the present invention, when administered to a patient, to prevent a disease from occurring and/or to cure or to alleviate disease symptoms, signs or causes. As such, to protect a patient from a disease includes both preventing disease occurrence (prophylactic treatment) and treating a patient that has a disease (therapeutic treatment). A beneficial effect can easily be assessed by one of ordinary skill in the art and/or by a trained clinician who is treating the patient. The term, "disease" refers to any deviation from the normal health of a mammal and includes a state when disease symptoms are present, as well as conditions in which a deviation has occurred, but symptoms are not yet manifested.

The following example is provided for the purpose of illustration and are not intended to limit the scope of the present invention.

EXAMPLES

Example 1

The following example shows that fat-laden hepatocytes are more prone to cellular necrosis than apoptosis when exposed to hydrophobic bile acids.

Hepatic steatosis is common in metabolic liver diseases, such as cystic fibrosis and tyrosinemia. There is now evidence that steatosis, regardless of etiology, may worsen liver injury. The effect of steatosis on the toxicity of bile acids, a mediator of cholestatic disease, has not been examined. The aim of this study was to determine if fat-laden hepatocytes were more susceptible to cell injury and oxidant stress caused by hydrophobic bile acids.

Briefly, 8-week-old obese Zucker (fa/fa) rats (Zucker rat model of hepatic steatosis) and lean (Fa/?) litter-mates were sacrificed. Liver blood tests and liver histology were obtained, and hepatocytes isolated by the recirculating collagenase perfusion technique. Initial trypan blue exclusion exceeded 94%. Cells were incubated in suspension with glycochenodeoxycholic acid (GCDC) (0,–1000 $\mu$M) in Krebs-Ringer-HEPES for 4 hours. Aliquots of cells were removed hourly for determination of: (1) hydroperoxide generation measured by fluorescence of dichlorofluororescin diacetate (DCF-DA) that was preloaded into hepatocytes; (2) %LDH release as a measure of cell necrosis; and (3) DAPI fluorescence microscopy of fixed cells to quantify apoptosis. Liver histology was quantitated using a grading system.

The results showed that obese rats had significantly increased baseline serum AST, ALT and AP (data not shown). Liver histology showed increased microvesicular steatosis and portal inflammation in obese compared to lean rats consistent with a baseline steatohepatitis. Surprisingly, apoptosis was significantly reduced in fat-laden isolated cells exposed to GCDC compared to lean cells (31% vs. 8%–100 $\mu$M GCDC×3 hours, p=0.008). In contrast, at concentrations of 100–1000 $\mu$M GCDC, necrosis (%LDH release) was significantly higher in fat-laden cells (54% vs. 24%–100 $\mu$M GCDC×3 hours, p=0.005). A trend was present towards increased generation of hydroperoxides in fat-laden cells exposed to GCDC.

These data demonstrate the novel observation that fat-laden hepatocytes are more prone to cell necrosis rather than apoptosis when exposed to hydrophobic bile acids, likely because of poor tolerance of fat-laden cells to increased oxidant stress. The implications of these findings are: a) that cell necrosis may be physiologically more important than apoptosis in the pathogenesis of steatohepatitis, especially in metabolic liver diseases; and b) that antioxidant therapy is expected to be of benefit in cholestatic metabolic liver disorders.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A pharmaceutical composition for treatment of a patient who has hepatic steatosis or steatohepatitis, or who has at least one symptom associated with hepatic steatosis or steatohepatitis, said composition consisting essentially of:
    a. soluble vitamin E in an amount of between about 10 international units per kilogram body weight of the patient per day (IU/kg/day) and about 20 IU/kg/day;
    b. mixed carotenoids in an amount of between about 0.1 milligram per kilogram body weight of the patient per day (mg/kg/day) and about 1 mg/kg/day; and,
    c. selenium in an amount of between about 0.5 microgram per kilogram body weight of the patient per day ($\mu$g/kg/day) and about 3 $\mu$g/kg/day.

2. The composition of claim 1, wherein said vitamin E is D-alpha tocopheryl polyethylene glycol-1000 succinate.

3. The composition of claim 1, wherein said mixed carotenoids comprise natural source water-dispersible $\beta$-carotene.

4. The composition of claim 1, wherein said selenium is sodium selenite pentahydrate.

5. The composition of claim 1, wherein said composition consists essentially of:
    a. the soluble vitamin E in an amount of between about 10 IU/kg/day and about 20 IU/kg/day;
    b. the mixed carotenoids in an amount of between about 0.2 mg/kg/day and about 0.5 mg/kg/day; and,
    c. the selenium in an amount of between about 1 $\mu$g/kg/day and about 2 $\mu$g/kg/day.

6. The composition of claim 1, wherein said composition consists essentially of:
    a. the soluble vitamin E at a concentration of from about 10 IU vitamin E per milliliter of the composition (10 IU/ml) to about 20 IU/ml;
    b. the mixed carotenoids at a concentration from about 0.1 mg per ml of the composition (0.1 mg/ml) to about 0.75 mg/ml; andm,
    c. the selenium at a concentration of from about 1 $\mu$g per ml of the composition (1 $\mu$g/ml) to about 5 $\mu$g/ml.

7. A pharmaceutical composition for treatment of a patient who has hepatic steatosis o steatohepatitis, or who has at least one symptom associated with hepatic steatosis or steatohepatitis, said composition comprising:
    a. soluble vitamin E in an amount of between about 10 international units per kilogram body weight of the patient per day (IU/kg/day) and about 100 IU/kg/day;
    b. mixed carotenoids in an amount of between about 0.1 milligram per kilogram body weight of the patient per day (mg/kg/day) and about 1 mg/kg/day;
    c. selenium in an amount of between about 0.5 microgram per kilogram body weight of the patient per day ($\mu$g/kg/day) and about 3 $\mu$g/kg/day; and,
    d. an agent selected from the group consisting of ursodeoxycholic add, tauro-ursodeoxycholic acid, and a derivative thereof selected from the group consisting of monosulfate and disulfate esters of ursodeoxycholic acid or tauro-ursodeoxycholic acid, derivatives thereof having increased solubility in water, and derivatives thereof that are useful for treating liver disease.

8. The composition of claim 7, wherein said composition consists essentially of:
    a. the soluble vitamin E in an amount of between about 25 IU/kg/day and about 50 IU/kg/day;
    b. the mixed carotenoids in an amount of between about 0.2 mg/kg/day and about 0.5 mg/kg/day;
    c. the selenium in an amount of between about 1 $\mu$g/kg/day and about 2 $\mu$g/kg/day; and
    d. the agent selected from the group consisting of ursodeoxycholic acid, tauro-ursodeoxycholic acid, and a derivative thereof selected from the group consisting of monosulfate and disulfate esters of ursodeoxycholic acid or tauro-ursodeoxycholic acid, derivatives thereof having increased solubility in water, and derivatives thereof that are useful for treating liver disease.

9. The composition of claim 7, wherein said agent is ursodeoxycholic acid.

10. The composition of claim 7, wherein said vitamin E is D-alpha tocopheryl polyethylene glycol-1000 succinate.

11. The composition of claim 7, wherein said mixed carotenoids comprise natural source water-dispersible $\beta$-carotene.

12. The composition of claim 7, wherein said selenium is sodium selenite pentahydrate.

13. The composition of claim 7, wherein said composition comprises:
   a. the soluble vitamin E in an amount of between about 25 IU/kg/day and about 75 IU/kg/day;
   b. the mixed carotenoids in an amount of between about 0.2 mg/kg/day and about 0.5 mg/kg/day;
   c. the selenium in an amount of between about 1 μg/kg/day and about 2 μg/kg/day; and
   d. the agent selected from the group consisting of ursodeoxycholic acid, tauro-ursodeoxycholic acid, and a derivative thereof selected from the group consisting of monosulfate and disulfate esters of ursodeoxycholic acid or tauro-ursodeoxycholic acid, derivatives thereof having increased solubility in water, and derivatives thereof that are useful For treating liver disease.

14. The composition of claim 7, wherein said vitamin E is water soluble.

15. A method of treating liver injury resulting from hepatic steatosis or steatohepatitis in a patient, said method comprising administering to a patient who has hepatic steatosis or steatohepatitis, or who has at least one symptom associated with said hepatic steatosis or steatohepatitis, a pharmaceutical composition consisting essentially of soluble Vitamin E, mixed carotenoids and selenium.

16. The method of claim 15, wherein said hepatic steatosis is nonalcoholic steatohepatitis.

17. The method of claim 15, wherein said composition consists essentially of;
   a. the soluble vitamin E in an amount of between about 10 international units per kilogram body weight of the patient per day (IU/kg/day) and about 100 IU/kg/day;
   b. the mixed carotenoids in an amount of between about 0.1 milligram per kilogram body weight of the patient per day (μg/kg/day) and about 1 mg/kg/day; and
   c. the selenium in an amount of between about 0.5 microgram per kilogram body weight of the patient per day (mg/kg/day) and about 3 μg/kg/day.

18. The method of claim 15, wherein said vitamin E is D-alpha tocopheryl polyethylene glycol-1000 succinate.

19. The method of claim 15, wherein said mixed carotenoids comprise natural source water-dispersible β-carotene.

20. The method of claim 15, wherein said selenium is sodium selenite pentahydrate.

21. The method of claim 15, wherein said composition consists essentially of:
   a. the soluble vitamin E in an amount of between about 25 IU/kg/day and about 75 IU/kg/day;
   b. the mixed carotenoids in an amount of between about 0.2 mg/kg/day and about 0.5 mg/kg/day; and,
   c. the selenium in an amount of between about 1 μg/kg/day and about 2 μg/kg/day.

22. The method of claim 15, wherein said composition consists essentially of:
   a. the soluble vitamin E in an amount of between about 25 IU/kg/day and about 50 IU/kg/day;
   b. the mixed carotenoids in an amount of between about 0.2 mg/kg/day and about 0.5 mg/kg/day; and,
   c. the selenium, in an amount of between about 1 μg/kg/day and about 2 μg/kg/day.

23. The method of claim 15, wherein said composition consists essentially of:
   a. the soluble vitamin E at a concentration of from about 20 IU vitamin E per milliliter of the composition (20 IU/ml) to about 75 IU/ml;
   b. the mixed carotenoids at a concentration from about 0.1 mg per ml of the composition (01 mg/ml) to about 0.75 mg/ml; and,
   c. the selenium at a concentration of from about 1 μg per ml of the composition (1 μg/ml) to about 5 μg/ml.

24. A method of treating liver injury resulting from hepatic steatosis or steatohepatitis in a patient, said method comprising administering to a patient who has hepatic steatosis or steatohepatitis, or who has at least one symptom associated with hepatic steatosis or steatohepatitis, a pharmaceutical composition comprising soluble Vitamin E, mixed carotenoids, selenium, and at least one additional agent for the treatment of liver injury resulting from hepatic steatosis or steatohepatitis, wherein said soluble vitamin E is administered in an amount of between about 10 international units per kilogram body weight of the patient per day (IU/kg/day) and about 100 IU/kg/day.

25. The method of claim 24, wherein said pharmaceutical composition comprises:
   a. the soluble vitamin E in an amount of between about 10 international units per kilogram body weight of the patient per clay (IU/kg/day) and about 100 IU/kg/day;
   b. the mixed carotenoids in an amount of between about 0.1 milligram per kilogram body eight of the patient per day (mg/kg/day) and about 1 mg/kg/day;
   c. the selenium in an amount of between about 0.5 microgram per kilogram body weight of the patient per day (μg/kg/day) and about 3 μg/kg/day; and
   d. the at least one additional agent for the treatment of liver injury resulting from hepatic steatosis or steatohepatitis.

26. The method of claim 24, wherein said agent for the treatment of hepatic steatosis or steatohepatitis is ursodeoxycholic acid, tauro-ursodeoxycholic acid or a derivative thereof selected from the group consisting of monosulfate and disulfate esters thereof, derivatives thereof having increased solubility in water, and deny that are useful for treating liver disease.

27. The method of claim 24, wherein said agent for the treatment of hepatic steatosis or steatohepatitis is ursodeoxycholic acid.

28. The method of claim 24, wherein said vitamin E is water soluble.

* * * * *